(12) United States Patent
Tokko et al.

(10) Patent No.: US 9,332,912 B2
(45) Date of Patent: May 10, 2016

(54) ELECTRONIC SPHYGMOMANOMETER FOR MEASURING BLOOD PRESSURE BASED ON ARTERIAL VOLUME CHANGE

(71) Applicant: OMRON HEALTHCARE Co., Ltd., Muko-shi, Kyoto (JP)

(72) Inventors: Yoshihide Tokko, Muko (JP); Yukiya Sawanoi, Muko (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 851 days.

(21) Appl. No.: 13/626,568

(22) Filed: Sep. 25, 2012

(65) Prior Publication Data
US 2013/0023777 A1    Jan. 24, 2013

Related U.S. Application Data

(63) Continuation of application No. PCT/JP2011/052509, filed on Feb. 7, 2011.

(30) Foreign Application Priority Data

Mar. 25, 2010    (JP) ................................. 2010-070089

(51) Int. Cl.
*A61B 5/02* (2006.01)
*A61B 5/021* (2006.01)
(Continued)

(52) U.S. Cl.
CPC ......... *A61B 5/02116* (2013.01); *A61B 5/02438* (2013.01); *A61B 5/7239* (2013.01)

(58) Field of Classification Search
CPC ........... A61B 5/02116; A61B 5/02438; A61B 5/7239; A61B 5/021; A61B 5/022; A61B 5/02255; A61B 5/02225
See application file for complete search history.

(56) References Cited

U.S. PATENT DOCUMENTS 4,524,777 A * 6/1985 Kisioka et al. ................. 600/490
2009/0312652 A1* 12/2009 Yamakoshi ........ A61B 5/02255
600/493

(Continued)

FOREIGN PATENT DOCUMENTS

JP    54-050175 A    4/1979
WO    2010/024129 A1   3/2010

OTHER PUBLICATIONS

International Search Report issued in corresponding International Application No. PCT/JP2011/052509 dated Apr. 19, 2011 and English translation thereof (2 pages).

(Continued)

*Primary Examiner* — Michael Kahelin
*Assistant Examiner* — Tho Tran
(74) *Attorney, Agent, or Firm* — Osha Liang LLP

(57) ABSTRACT

Every pulse wave, a constant volume control unit performs servo control while updating a servo gain such that a difference between an arterial volume shown by an arterial volume signal that is detected by an arterial volume detection circuit and a control target value of the servo control is less than a control deviation at which a rate of change of the arterial volume relative to a change in cuff pressure is deemed to be constant. Because the control deviation is the difference between the arterial volume shown by the arterial volume signal and the control target value, a blood pressure decision unit decides, as a blood pressure, the cuff pressure sequentially detected in a period during which servo control is performed, by correcting the cuff pressure using the control deviation and the rate of change deemed to be constant.

7 Claims, 9 Drawing Sheets

(51) Int. Cl.
*A61B 5/024* (2006.01)
*A61B 5/00* (2006.01)

(56) References Cited

U.S. PATENT DOCUMENTS

2011/0208069 A1    8/2011  Sawanoi et al.
2011/0282220 A1*  11/2011  Tokko et al. .................. 600/493
2011/0301476 A1*  12/2011  Sawanoi et al. ............... 600/494

OTHER PUBLICATIONS

Yamakoshi et. al., "Indirect Measurement of Instantaneous Arterial Blood Pressure in the Human Finger by the Vascular Unloading Technique," IEEE Transactions on Biomedical Engineering, vol. BME-27, No. 3, Mar. 1980, pp. 150-155 (6 pages).

* cited by examiner

ELECTRONIC SPHYGMOMANOMETER FOR
MEASURING BLOOD PRESSURE BASED ON
ARTERIAL VOLUME CHANGE

TECHNICAL FIELD

This invention relates to an electronic sphygmomanometer, and more particularly to an electronic sphygmomanometer for continuously measuring blood pressure every heartbeat while detecting change in arterial volume.

BACKGROUND ART

With a conventional electronic sphygmomanometer, an arm band (cuff) is wrapped around a measurement site, the pressure inside the cuff (cuff pressure) is increased to greater than the highest blood pressure, and a pulse produced by an artery is detected with a pressure sensor via the cuff in a subsequent process of gradually reducing the cuff pressure, with the highest blood pressure and the lowest blood pressure being decided utilizing the cuff pressure and the magnitude of the pulse (pulse wave amplitude) at that time (oscillometric method). In contrast, a sphygmomanometer employing a volume compensation method that is configured to continuously measure blood pressure every heartbeat in a noninvasive manner has been developed (Patent Literature 1).

The volume compensation method involves continuously detecting blood pressure values by compressing an artery with a cuff from outside the body, equalizing the compression pressure (cuff pressure) with arterial pressure, that is, blood pressure, by keeping the volume per unit length of the pulsating artery constant, and detecting the cuff pressure when this state is maintained. In the volume compensation method, the volume (control target value "V0") of the artery in a state where the arterial pressure is in equilibrium with the cuff pressure exerted on the artery, that is, when the arterial wall is in an unloaded state, is detected in advance. The cuff pressure is controlled such that the artery volume which changes depending on the pulse per heartbeat matches the control target value V0 (servo control).

With conventional servo control, PID control for controlling the cuff pressure is used, using the difference between an arterial volume signal (DC component of volume pulse wave) and a target arterial volume signal as a feedback signal. With this control method, increasing the control gain until an arterial volume change signal (AC component of volume pulse wave) is less than or equal to −15 dB of the gain at the time of the maximum amplitude is said to enable a blood pressure measurement error of approximately 5% to be achieved (Non-Patent Literature 1).

Patent Literature 1: JP 54-50175A

Non-Patent Literature

Non-patent literature 1: Indirect Measurement of Instantaneous Arterial Blood Pressure in the Human Finger by the Vascular Unloading Technique; KEN-ICHI YAMAKOSHI, HIDEAKI SHIMAZU, AND TATSUO TOGAWA (IEEE TRANSACTIONS ON BIOMEDICAL ENGINEERING, VOL. BME-27, NO. 3, MARCH 1980)

SUMMARY OF INVENTION

PID control, which is feedback control, is used as the servo control method (denotes control that combines proportional control, integral control and derivative control and converges on a control target value). That is, a value obtained by respectively multiplying the deviation between the current arterial volume signal and a control target value derived in advance, the integral of the deviation, and the derivative of the deviation by a given constant (hereinafter, servo gain) and summing the resultant values is output as the control amount. In order to perform highly accurate blood pressure measurement, the optimal value of the servo gain needs to be adjusted in accordance with the control target.

However, because a characteristic of PID control is that oscillations occur in the response of the cuff pressure control system as a result of raising the servo gain, blood pressure measurement error cannot be completely eliminated. Also, because the control target changes for every subject, it is difficult to adjust the servo gain so that oscillations do not occur. Furthermore, in order for the control system to respond to the blood pressure waveform without delay, a pump, a valve and the like that are able to control a high flow rate are needed, increasing the size of the electronic sphygmomanometer.

Hence, one or more embodiments of the present invention provide an electronic sphygmomanometer that is able to accurately measure blood pressure based on the change in arterial volume, without giving rise to an increase in device size.

An electronic sphygmomanometer according to one or more embodiments of the present invention includes a cuff that is placed on a blood pressure measurement site, a pressure detection unit for detecting a cuff pressure representing a pressure inside the cuff, a volume detection unit provided in the cuff and for detecting an arterial volume signal showing an arterial volume of the measurement site in a process of changing the cuff pressure, a cuff pressure adjustment unit for adjusting the cuff pressure by pressurization and depressurization, and a blood pressure measurement unit.

The blood pressure measurement unit includes a control target value detection unit that detects, as a control target value, a value of the arterial volume signal when an amplitude of the arterial volume signal detected by the volume detection unit indicates a maximum, a rate-of-change detection unit that sequentially detects a rate of change in the arterial volume in the process of changing the cuff pressure, based on the arterial volume signal detected by the volume detection unit, a control deviation detection unit that detects, as a control deviation, a difference between the value of the arterial volume signal and the control target value, a servo control unit for performing servo control on the cuff pressure adjustment unit using a servo gain, such that the value of the arterial volume signal matches the control target value, and a blood pressure decision unit that decides, as a blood pressure, the cuff pressure sequentially detected by the pressure detection unit in a period during which the servo control is performed, by correcting the cuff pressure using the control deviation and a rate of change that is deemed to be constant, and the servo control unit updates the servo gain every pulse wave, such that the control deviation, which is the difference between the value of the arterial volume signal detected by the volume detection unit and the control target value, indicates a value that is less than a control deviation target value, which is the control deviation detected by the control deviation detection unit in a period during which the rate of change sequentially detected by the rate-of-change detection unit is deemed to be constant.

According to one or more embodiments of the present invention, the blood pressure decision unit calculates a correction value, by dividing the control deviation by the rate of change that is deemed to be constant, and corrects the cuff pressure by adding the correction value to the cuff pressure.

According to one or more embodiments of the present invention, the period during which the rate of change is deemed to be constant denotes a period during which a rate of change that is greater than or equal to a prescribed threshold is detected with respect to rates of change detected by the rate-of-change detection unit when the maximum value of the amplitude of the arterial volume signal is detected.

According to one or more embodiments of the present invention, the period during which the rate of change is deemed to be constant denotes a period in which a difference in rates of change is less than or equal to a prescribed threshold, with respect to rates of change detected by the rate-of-change detection unit when the value of the arterial volume signal indicates the control target value.

According to one or more embodiments of the present invention, the blood pressure measurement unit includes a detection unit that detects, as an initial control cuff pressure, the cuff pressure detected when the amplitude of the arterial volume signal detected by the volume detection unit is a maximum value. The servo control unit starts the servo control, such that the value of the arterial volume signal matches the control target value, after the cuff pressure is set to the initial control cuff pressure by the cuff pressure adjustment unit.

According to one or more embodiments of the present invention, the process of changing the cuff pressure denotes a process of increasing the cuff pressure or a process of reducing the cuff pressure.

According to one or more embodiments of the present invention, a blood pressure measurement program for measuring blood pressure while detecting an arterial volume signal showing an arterial volume of a blood pressure measurement site in a process of changing a cuff pressure representing a pressure inside a cuff that is placed on the measurement site causes a computer to execute the steps of detecting, as a control target value, a value of the arterial volume signal when an amplitude of the detected arterial volume signal indicates a maximum, sequentially detecting a rate of change in the arterial volume in the process of changing the cuff pressure, based on the detected arterial volume signal, detecting, as a control deviation, a difference between the value of the arterial volume signal and the control target value, performing servo control on a cuff pressure adjustment unit using a servo gain, such that the value of the arterial volume signal matches the control target value, and deciding, as a blood pressure, the cuff pressure sequentially detected in a period during which the servo control is performed, by correcting the cuff pressure using the control deviation and a rate of change that is deemed to be constant. In the step of performing servo control, the servo gain is updated every pulse wave, such that the control deviation, which is the difference between the value of the detected arterial volume signal and the control target value, indicates a value that is less than a control deviation target value, which is the control deviation detected in a period during which the sequentially detected rate of change is deemed to be constant.

According to one or more embodiments of the present invention, servo control is performed while updating a servo gain every pulse wave, such that the difference between the arterial volume shown by an arterial volume signal detected by a volume detection unit and a control target value of the servo control is less than a control deviation target value. Given that the control deviation is the difference between the arterial volume shown by the arterial volume signal detected in a period during which the rate of change detected by a rate-of-change detection unit is deemed to be constant and the control target value, the cuff pressure sequentially detected by a pressure detection unit in the period during which servo control is performed can be decided as the blood pressure, by correcting the cuff pressure using the control deviation and the rate of change deemed to be constant.

Accordingly, blood pressure can be measured accurately based on the change in arterial volume, without giving rise to an increase in the size of the cuff pressure adjustment unit, because servo control is performed while allowing a control deviation.

DETAILED DESCRIPTION OF INVENTION

Figure 1:
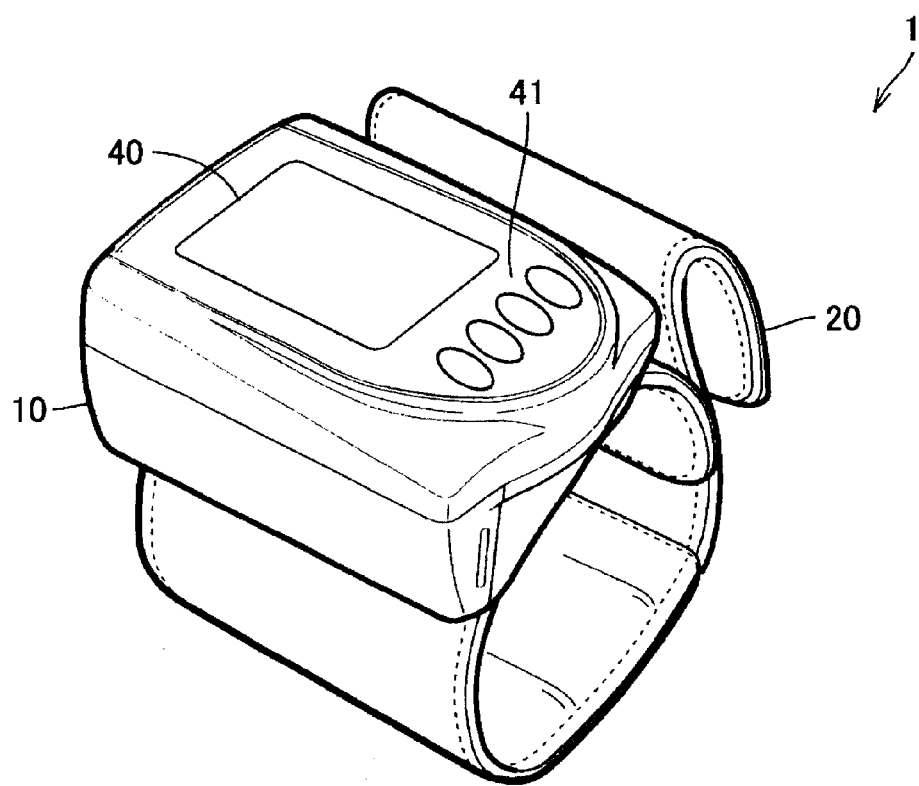
FIG. 1 is an external perspective view of an electronic sphygmomanometer according to an embodiment.

An embodiment of the present invention will be described in detail, with reference to the drawings. Note that the same reference signs are given to portions that are the same or equivalent in the drawings, and description thereof will not be repeated.

External Appearance

FIG. 1 is an external perspective view of an electronic sphygmomanometer 1 according to an embodiment of the present invention.

Referring to FIG. 1, the electronic sphygmomanometer 1 is provided with a main body unit 10 and a cuff 20 that is capable of being wrapped around a prescribed measurement site of the person being measured. The main body unit 10 is attached to the cuff 20. A display unit 40 is constituted by liquid crystal, for example, and an operation unit 41 that is operated in order to receive instructions from a user (e.g., person being measured) are disposed on the surface of the main body unit 10. The operation unit 41 includes a plurality of switches.

In the present embodiment, the measurement site is described as being the wrist. However, the measurement site is not limited to the wrist and may be the upper arm, for example. In the present embodiment, there is only one measurement site.

With the electronic sphygmomanometer 1 in the present embodiment, the main body unit 10 is attached to the cuff 20, as shown in FIG. 1. However, a configuration may be adopted in which a separate main body unit 10 and cuff 20 are connected by an air tube (air tube 31 in FIG. 2), such as adopted in an upper arm-type electronic sphygmomanometer.

Hardware Configuration

Figure 2:
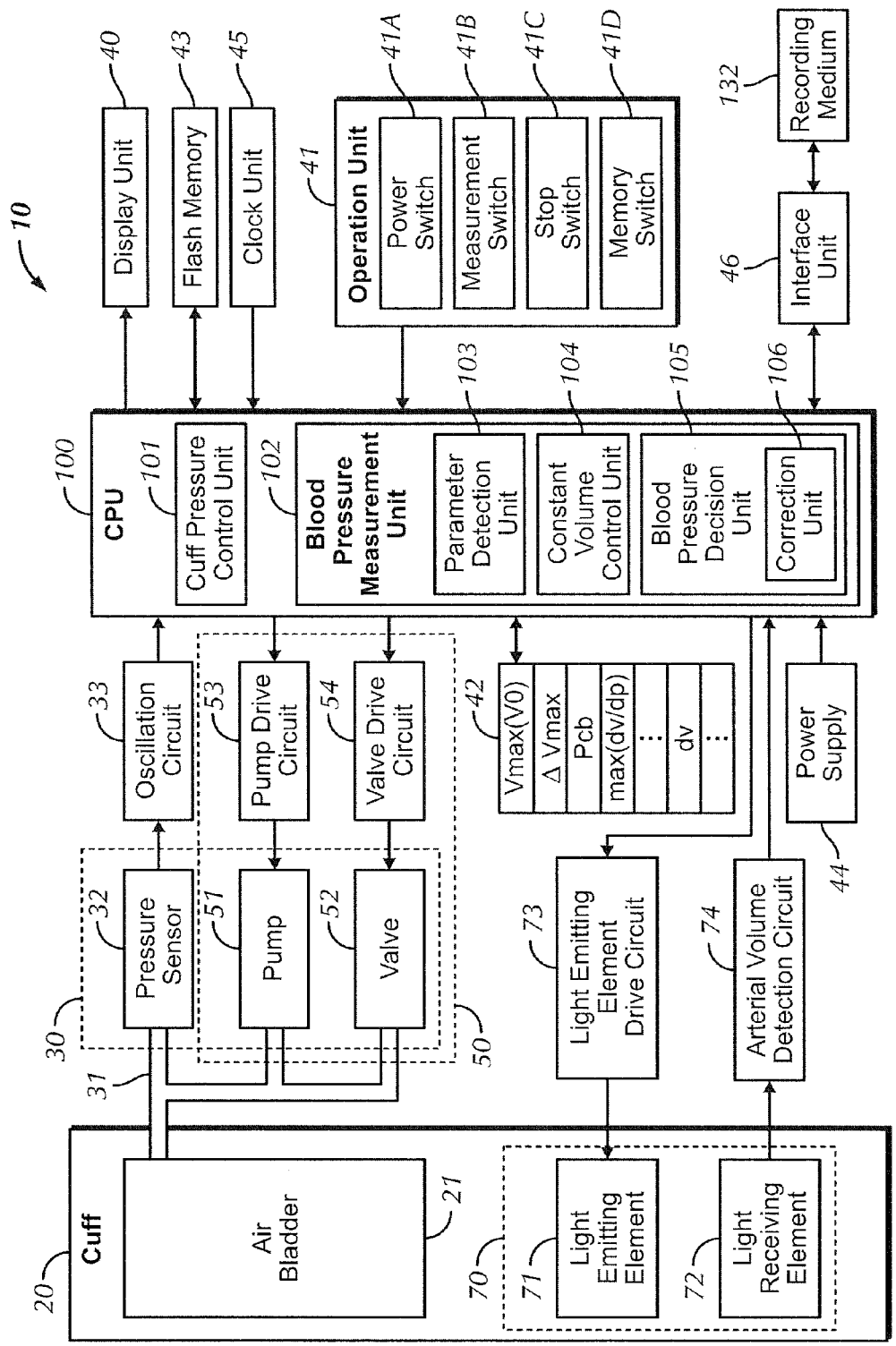
FIG. 2 is a block diagram showing an exemplary configuration of the electronic sphygmomanometer according to the embodiment.

FIG. 2 is a block diagram showing an exemplary configuration of the electronic sphygmomanometer 1 according to an embodiment of the present invention.

Referring to FIG. 2, the cuff 20 of the electronic sphygmomanometer 1 includes an air bladder 21 and an arterial volume sensor 70. The arterial volume sensor 70 has a light emitting element 71 and a light receiving element 72. The light emitting element 71 irradiates light onto an artery, and the light receiving element 72 receives light irradiated by the light emitting element 71 that has passed through or been reflected by the artery. The light emitting element 71 and the light receiving element 72 are disposed at a predetermined interval on the inner side of the air bladder 21, for example.

The arterial volume sensor 70 can be any sensor that is able to detect the volume of an artery, and may be a sensor that detects the volume of an artery using an impedance sensor (impedance plethysmograph). In this case, a plurality of electrodes for detecting the impedance of a site that includes an artery (electrode pair for applying current and electrode pair for detecting voltage) are included, in place of the light emitting element 71 and the light receiving element 72.

The air bladder 21 is connected to an air system 30 via the air tube 31. In addition to the abovementioned display unit 40 and operation unit 41, the main body unit 10 includes the air system 30, a CPU (Central Processing Unit) 100 for centrally controlling the units and performing various arithmetic operations, a memory unit 42 for storing various data and programs for causing the CPU 100 to perform prescribed operations, a nonvolatile memory (e.g., flash memory) 43 for storing measurement results and the like, a power supply 44 for supplying power to units such as the CPU 100, a clock unit 45 that performs clock operations, and an interface unit 46 for reading out and writing programs and data from and to a detachable recording medium 132. The functional units of the CPU 100 will be discussed later.

The operation unit 41 includes a power switch 41A that receives input of an instruction for turning power supply on or off, a measurement switch 41B for receiving a measurement start instruction, a stop switch 41C for receiving a measurement stop instruction, and a memory switch 41D for receiving an instruction to read out information such as blood pressure recorded in the flash memory 43.

The air system 30 includes a pressure sensor 32 for detecting the pressure inside the air bladder 21 (cuff pressure Pc), a pump 51 for supplying air to the air bladder 21 in order to increase the cuff pressure Pc, and a valve 52 that opens and closes in order to discharge air from or enclose air in the air bladder 21.

The main body unit 10 further includes a light emitting element drive circuit 73, an arterial volume detection circuit 74, and an oscillation circuit 33, a pump drive circuit 53 and a valve drive circuit 54 in association with the above air system 30.

The light emitting element drive circuit 73 causes the light emitting element 71 to emit light at a prescribed timing according to a command signal from the CPU 100. The arterial volume detection circuit 74 detects the arterial volume by converting the output from the light receiving element 72 into a voltage value. The detected arterial volume is output to the CPU 100 as an arterial volume signal.

The pressure sensor 32 is a capacitance pressure sensor, for example, and the capacitance value changes with cuff pressure Pc. The oscillation circuit 33 outputs an oscillation frequency signal that depends on the capacitance value of the pressure sensor 32 to the CPU 100. The CPU 100 detects pressure by converting the signal obtained from the oscillation circuit 33 into a pressure. The pump drive circuit 53 controls the drive of the pump 51 based on a control signal provided from the CPU 100. The valve drive circuit 54 controls the opening and closing of the valve 52 based on a control signal provided from the CPU 100.

The pump 51, the valve 52, the pump drive circuit 53 and the valve drive circuit 54 constitute an adjustment unit 50 for adjusting the pressure inside the cuff 20 by pressurization or depressurization. The number of rotations and the direction of rotation of the pump 51 are controlled based on a voltage signal provided from the pump drive circuit 53, and the opening and closing operation of the valve 52 is controlled based on a voltage signal provided from the valve drive circuit 54. Note that the device constituting the adjustment unit 50 is not limited to the above. For example, in addition to the above, the adjustment unit 50 may include an air cylinder and an actuator for driving an air cylinder.

Although a configuration is adopted in which the air bladder 21 is included in the cuff 20, the fluid supplied to the cuff 20 is not limited to air, and may be a liquid or a gel, for example. Alternatively, the substance is not limited to fluid, and may be uniform particulates such as microbeads.

The electronic sphygmomanometer 1 measures blood pressure continuously by keeping the volume of the artery roughly constant.

Principles of Blood Pressure Measurement According to a Typical Volume Compensation Method Prior to describing the blood pressure measurement method of the present embodiment, the principles of blood pressure measurement according to a typical volume correction method will be described.

Operations such as the following are performed when measuring blood pressure in accordance with a typical volume compensation method. That is, external pressure is applied to an artery from outside the body, and the arterial wall is maintained in an unloaded state by performing control such that the external pressure on the body and the arterial pressure (blood pressure) are constantly in equilibrium. With a typical volume compensation method, blood pressure is measured by measuring the external pressure on the body at that time (unloaded state).

In actual fact, the external pressure on the body is equivalent to the cuff pressure Pc of the cuff 20 wrapped around the measurement site. Also, at the time of measurement, arterial volume "V0" when the cuff pressure Pc and blood pressure are in equilibrium is detected, and the cuff pressure Pc is controlled such that the arterial volume, which changes with variation in blood pressure, matches V0 (servo control).

Figure 3:
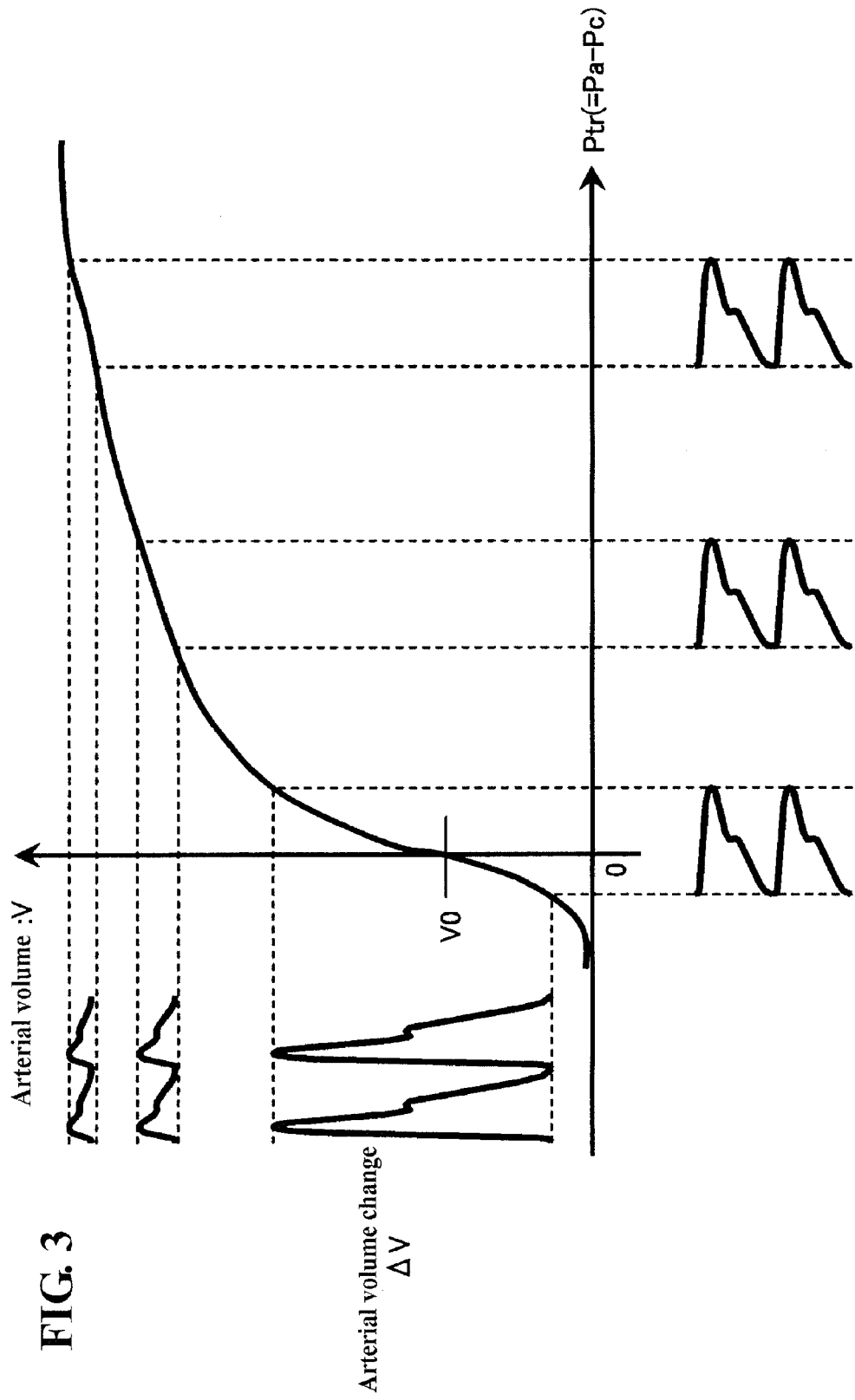
FIG. 3 is a graph showing mechanical properties of an artery.

FIG. 3 is a graph showing the mechanical properties of an artery. The graph in FIG. 3 shows the relationship between an arterial pressure-external pressure differential Ptr and an arterial volume V, with the arterial pressure-external pressure differential Ptr on the horizontal axis and the arterial volume V on the vertical axis. The arterial pressure-external pressure differential Ptr shows the difference between the arterial pressure Pa and the cuff pressure (external pressure on the body) Pc.

As shown in this graph, the mechanical properties of an artery typically show high nonlinearity. When the arterial pressure-external pressure differential Ptr is 0 (equilibrium state), that is, when the arterial wall is in an unloaded state, the compliance of the artery (amount of change in volume due to pulse) will be at its maximum. In other words, the ability of volume change to track pressure change will be at its maximum.

With a typical volume compensation method, the CPU 100 variably controls the level of the voltage signals provided to the pump 51 and the valve 52, such that the arterial volume detected by the pressure sensor 32 always indicates the capacitance value V0 at the point in time at which the arterial pressure-external pressure differential Ptr reverts to 0 (PID control). Blood pressure is thereby measured while the external pressure on the body (cuff pressure) is sequentially controlled. The arterial volume V0 in the case where the cuff pressure and the arterial pressure (blood pressure) are in equilibrium is thus the target value of servo control in a typical volume compensation method. In the present embodiment, the arterial volume V0 is also referred to as "equilibrium control target value V0".

According to the measurement principles of such a volume compensation method, in the case of not using a pump 51 having a high flow rate, as mentioned above, an oscillation phenomenon occurs in the response of the system for controlling the cuff pressure Pc, and blood pressure measurement error cannot be completely eliminated.

Principles of Blood Pressure Measurement according to the Present Embodiment

Blood pressure changes between systolic blood pressure (SYS) and diastolic blood pressure (DIA) every heartbeat. In the case where the cuff pressure Pc is fixed at a prescribed pressure, the arterial volume changes with a change in blood pressure (arterial volume change ΔV in FIG. 3). Because the mechanical properties of an artery have a nonlinear character as shown in FIG. 3, the size of the arterial volume change ΔV differs depending on the cuff pressure Pc, but the amount of change remains the same at 1 to 1 with the pulse pressure (=systolic arterial pressure−diastolic blood pressure). Also, in the case where the arterial volume is sufficiently close to the equilibrium control target value V0, the rate of change in arterial volume relative to the change in cuff pressure is deemed to be constant, and a pulse wave having an amplitude that enables blood pressure measurement can be detected in this period.

Accordingly, in the present embodiment, rather than fixing the control target value to the arterial volume (equilibrium control target value) V0 at which point the cuff pressure Pc and the arterial pressure are in equilibrium, the blood pressure value is measured after adjusting the servo gain, while allowing a control deviation of less than or equal to a prescribed value (control deviation target value discussed later).

Here, the control deviation is an arterial volume that is sufficiently close to the equilibrium control target value V0, and is equivalent to the difference between an arterial volume at which the rate of change in arterial volume relative to the change in the cuff pressure Pc is deemed to be constant and the equilibrium control target value V0.

In the servo control, when a control deviation is allowed, the cuff pressure Pc no longer tracks the arterial volume change ΔV, and error is included in the measured blood pressure as a result. Here, error denotes a difference between a blood pressure value detected in a state where the arterial volume V matches the equilibrium control target value V0 (unloaded state) and a blood pressure value measured while allowing a control deviation. Hereinafter, this error will be referred to as "blood pressure error Er".

In the present embodiment, an accurate blood pressure value is measured by deciding the servo gain while allowing a control deviation, and using the blood pressure error Er to correct blood pressure values measured in the period during which servo control is performed on the cuff pressure Pc using the decided servo gain. Also, because an accurate blood pressure value can be measured even while allowing a control deviation, volume change is not required to track pressure change perfectly, that is, improvement (enlargement) of the air system consisting of the pump 51 and the valve 52 is also not needed.

Control Deviation Target Value

Figure 4:
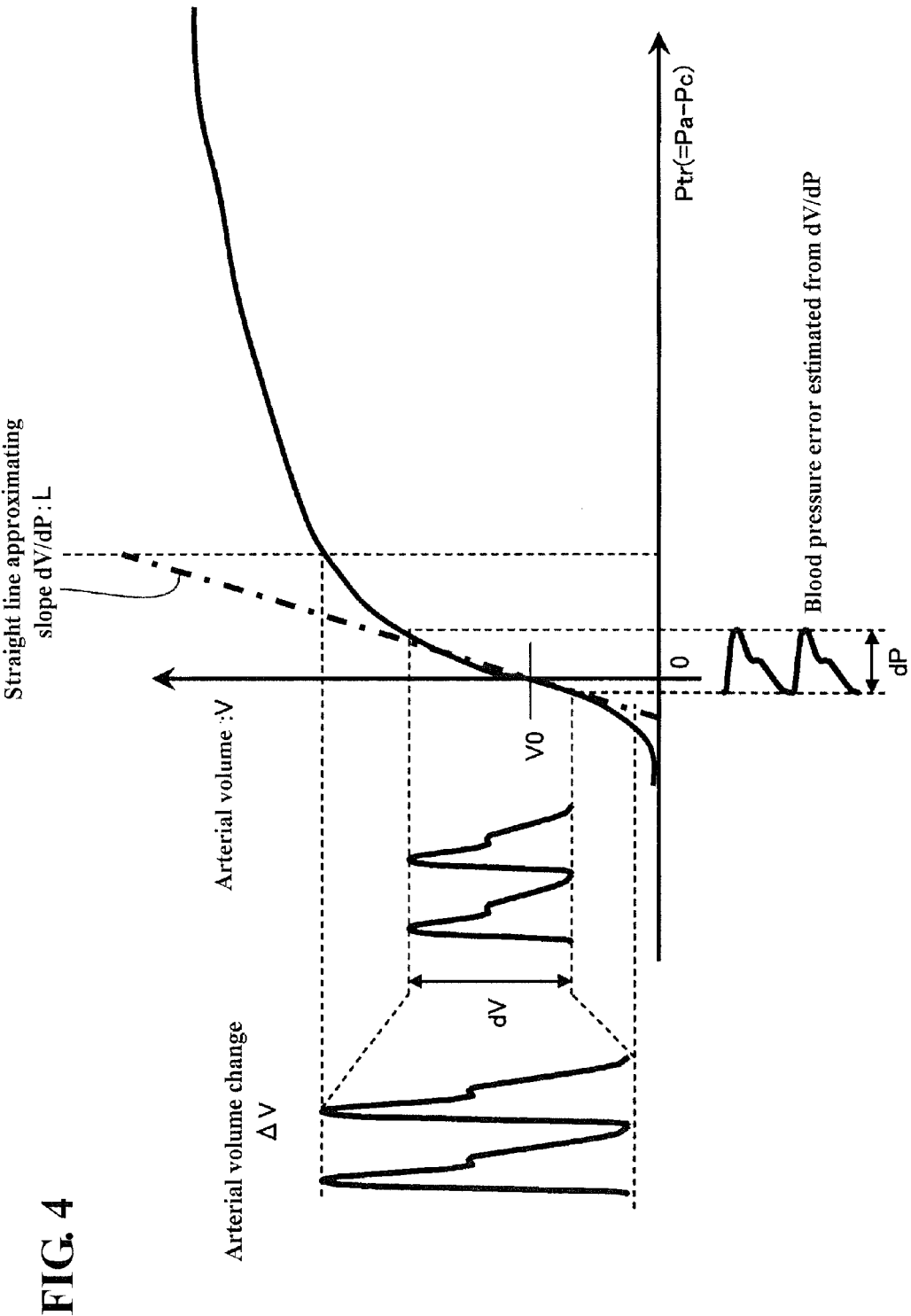
FIG. 4 is a diagram showing the amount of change in arterial volume relative to the amount of change in an arterial pressure-external pressure differential according to the embodiment.

FIG. 4 is a graph based on tests carried out by the inventors using the electronic sphygmomanometer 1. Test results in the case where the cuff 20 was placed on the measurement site in a state where the cuff pressure Pc was zero, and inflated at a constant low speed of 3 mm Hg/sec, for example, are shown.

In the graph, the relationship between the arterial pressure-external pressure differential Ptr and the arterial volume V is shown by the solid line curve, with the arterial pressure-external pressure differential Ptr on the horizontal axis and the arterial volume V on the vertical axis. Also, a slope dV/dP of the solid line curve is approximated by a dashed straight line L. The straight line L shows the relationship of the amount of change in the arterial volume V relative to the amount of change in the arterial pressure-external pressure differential Ptr.

As shown in FIG. 4, the inventors found that the solid line curve cannot be approximated by the straight line L in the case where tracking due to servo control is not sufficient, resulting in a large arterial volume change ΔV, but that in the case where tracking due to servo control is sufficient, resulting in the arterial volume change ΔV decreasing and the arterial volume V indicating the equilibrium control target value V0 or a value very close to the equilibrium control target value V0, the solid line curve can be approximated by the straight line L; that is, the rate of change in the arterial volume V relative to the change in the cuff pressure Pc is deemed to be regarded as substantially constant. Also, the inventors found that in the interval in which the solid line curve can be approximated by the straight line L, the blood pressure error Er (equivalent to difference pressure dP in FIG. 4) can be estimated based on the slope dV/dP.

Based on these findings, the inventors found that, in the period during which the solid line curve can be approximated by the straight line L, the measured blood pressure can be corrected to an accurate blood pressure using the blood pressure error Er, that is, a blood pressure equivalent to the blood pressure measured in a state where the arterial volume V matches the equilibrium control target value V0 (unloaded state) can be calculated.

In FIG. 4, the equilibrium control target value V0 is detected as follows. In other words, when air has been exhausted from the air bladder 21 and the cuff 20 has been wrapped around the measurement site in a state where the cuff pressure Pc is zero, the CPU 100 controls the pump drive circuit 53 to send air gradually to the air bladder 21 using the pump 51. In other words, air is sent to the air bladder 21, such that the cuff pressure Pc is increased at a constant low speed of around 3 mm Hg/sec, for example. In this pressurization process, the CPU 100 detects the amount of change per heartbeat in the amplitude of the arterial volume signal detected via the arterial volume detection circuit 74 (arterial volume change ΔV), and detects the point in time at which the arterial volume change ΔV is maximized. The average value of the arterial volume signal detected at that point in time is calculated and stored in a prescribed area of the memory unit 42, taking the calculated average value as the equilibrium control target value V0.

The average value of the arterial volume signal is equivalent to the value of the direct current component of the arterial volume signal, and the CPU 100 detects the equilibrium control target value V0 by filtering the arterial volume signal.

The slope dV/dP indicating the amount of change in the arterial volume relative to the amount of change in the arterial pressure-external pressure differential Ptr is calculated based on the detected average value of the arterial volume signal and the cuff pressure Pc detected at that time. In the present embodiment, the slope dV/dP used for blood pressure correction is calculated using the cuff pressure Pc at the time at which the equilibrium control target value V0 is detected. In the present embodiment, the value (blood pressure error Er) used for correction can be acquired by dividing the control deviation detected by servo control by the slope dV/dP. Although the actual slope dV/dP shows nonlinearity, such correction is possible because the slope dV/dP in the vicinity of the equilibrium control target value V0 can be approximated by the straight line L if the control deviation is small (refer to FIG. 4).

To perform the above correction, servo control needs to be performed on the cuff pressure Pc so that the control deviation is less than or equal to a prescribed value, such that the slope dV/dP in the vicinity of the equilibrium control target value V0 can be approximated by the straight line L. This prescribed value denotes a control deviation target value, which will be discussed later.

Figure 5:
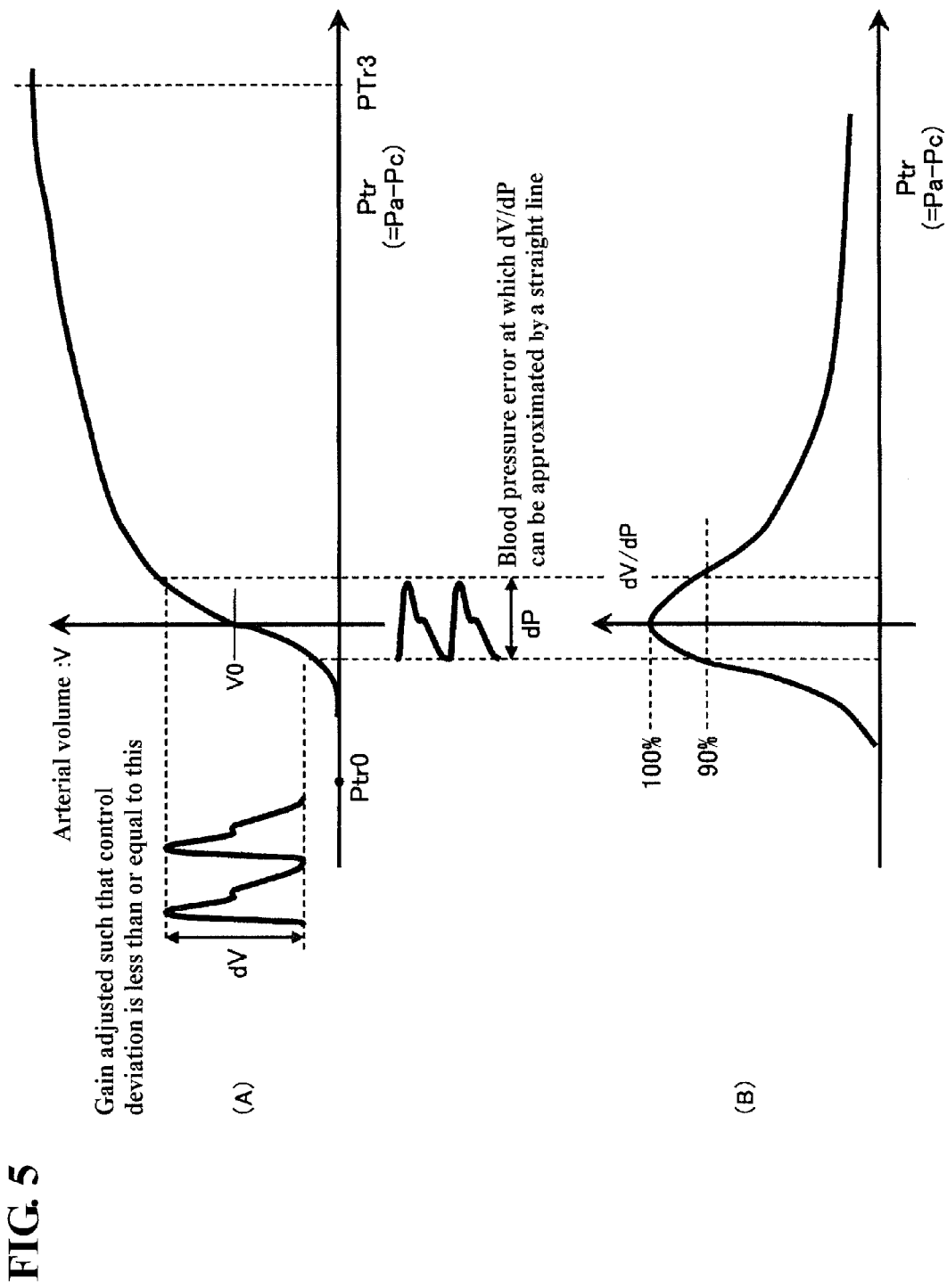
FIG. 5 is a diagram illustrating a method for deciding a control deviation target value according to the embodiment.

The method for deciding the control deviation target value will be described with reference to FIG. 5. The graph in FIG. 4 is shown in (A) of FIG. 5, and the change in the slope dV/dP of the graph (solid line curve) showing the relationship between the arterial pressure-external pressure differential Ptr and the arterial volume V in (A) of FIG. 5 is shown in (B) of FIG. 5. The graph in (B) of FIG. 5 is calculated by differentiating the graph in (A) of FIG. 5 with the arterial pressure-external pressure differential Ptr.

The rate of change, relative to the change in the cuff pressure Pc, of the arterial volume detected in the period between when the abovementioned maximum (100%) rate of change is detected in the pressurization process and when a rate of change of a magnitude less than or equal to a prescribed value (e.g., less than or equal to 10%) of the maximum (100%) rate of change is detected could be deemed to be constant. The optimal value is, however, not limited to a value of 10%.

In view of this, the value of a slope dV/dP equivalent to 90% of the case where the slope dV/dP corresponding to the equilibrium control target value V0 in (B) of FIG. 5 (maximum value of slope dV/dP) is taken as 100% is calculated, the difference between the arterial volume corresponding to the 100% slope dV/dP (equilibrium control target value V0) and the arterial capacitance value V corresponding to the 90% slope dV/dP is calculated, and the calculated difference is decided as the control deviation target value.

Figure 6:
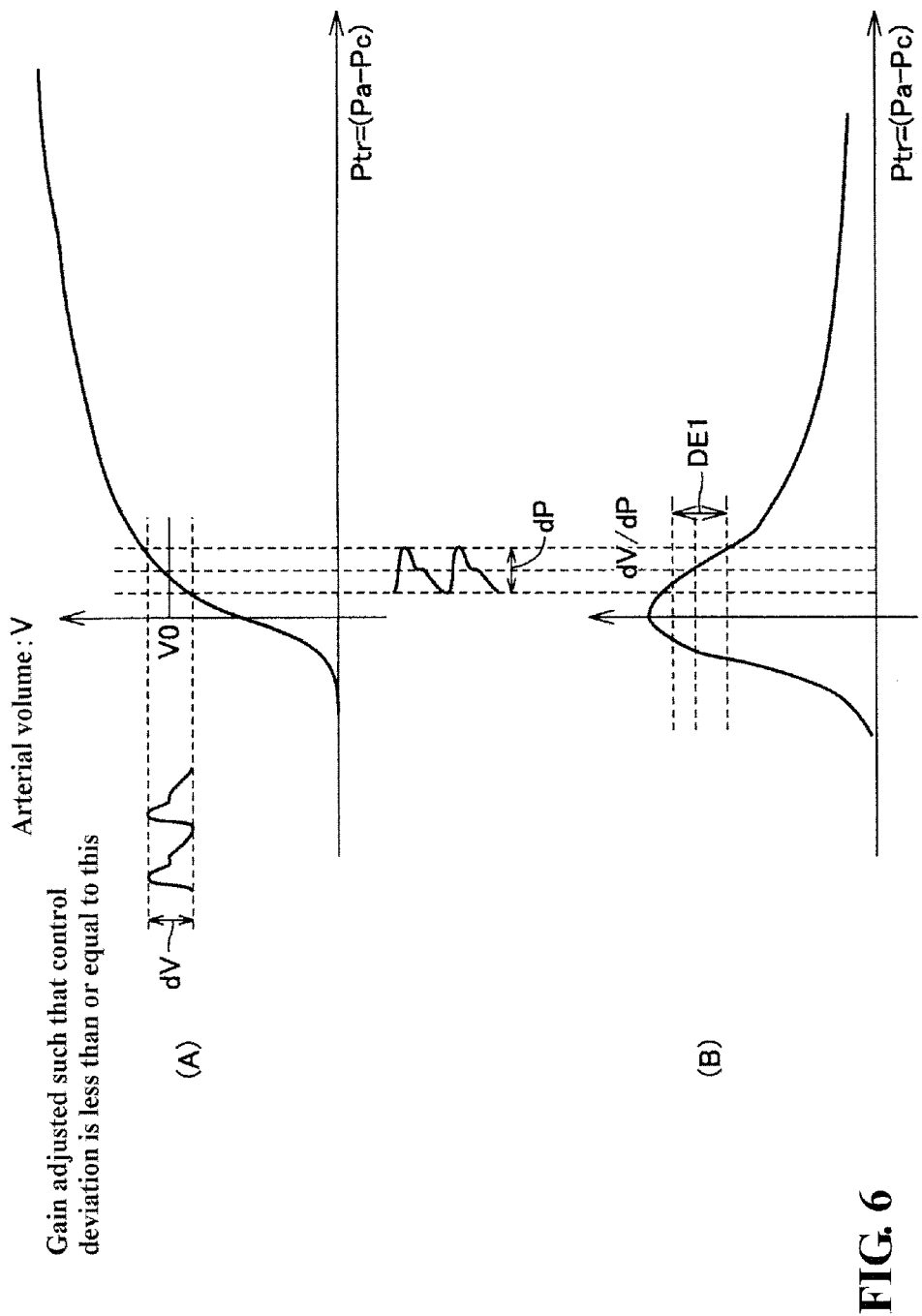
FIG. 6 is a diagram illustrating another method for deciding a control deviation target value according to the embodiment.

The method for deciding (detecting) the control deviation target value may be another method as shown in FIG. 6, for example. The graph in FIG. 4 is shown in (A) of FIG. 6, and the change in the slope dV/dP of the graph (solid line curve) showing the relationship between the arterial pressure-external pressure differential Ptr and the arterial volume V in (A) of FIG. 6 is shown in (B) of FIG. 6. The graph in (B) of FIG. 6 is calculated by differentiating the graph in (A) of FIG. 6 with the arterial pressure-external pressure differential Ptr.

With this decision method, the value of the arterial volume signal detected in a period during which the slope dV/dP can be approximated by a straight line in the pressurization process, that is, a period during which the rate of change of the detected arterial volume signal relative to the change in the cuff pressure Pc is deemed to be constant is taken as a control target value. The slope dV/dP detected when the value of the arterial volume signal indicates the control target value is set as a reference. The arterial capacitance value V corresponding to a slope dV/dP at which a difference DE1 from the reference slope dV/dP is less than or equal to a prescribed threshold (e.g., 5%) is then detected. The difference between this detected arterial capacitance value V and the arterial capacitance value V corresponding to the reference slope dV/dP is then calculated, and the calculated difference is decided as the control deviation target value. Note that the prescribed threshold is not limited to 5%.

At the time of the blood pressure measurement of the present embodiment, servo control is performed while the servo gain is updated, such that the control deviation is less than or equal to the control deviation target value.

Functional Configuration

The functional configuration of the CPU 100 is also shown in FIG. 2.

Referring to FIG. 2, the CPU 100 is provided with a cuff pressure control unit 101 that variably controls the cuff pressure Pc by controlling the pump drive circuit 53 and the valve drive circuit 54, and a blood pressure measurement unit 102 for measuring blood pressure.

The blood pressure measurement unit 102 includes a parameter detection unit 103 corresponding to an equilibrium control target value detection unit and a rate-of-change (slope dV/dP) detection unit, a constant volume control unit 104 equivalent to a servo control unit that performs servo control while updating the servo gain, and a blood pressure decision unit 105 equivalent to a blood pressure decision unit. The blood pressure decision unit 105 has a correction unit 106 that calculates the blood pressure error Er and corrects blood pressure. Each unit is constituted by a program. The programs are stored in the memory unit 42, and the function of each unit is realized by the CPU 100 reading out a program from the memory unit 42 and executing the instruction code of the read program.

Detection of Control Parameters

The parameter detection unit 103 detects the arterial volume signal via the arterial volume detection circuit 74, in the period during which the cuff pressure is gradually increased at a low speed of around 3 mm Hg/sec by the cuff pressure control unit 101. In this pressurization process, the change per heartbeat of the arterial volume signal ($\Delta V$), that is, the arterial volume change signal, is detected, and a point MAX at which that arterial volume change signal is at its maximum (amplitude of the arterial volume signal is at its maximum) is detected. The average value of the arterial volume signal per heartbeat at the point in time at which the maximum point MAX is detected is decided as the equilibrium control target value V0 and stored in a prescribed area of the memory unit 42. Also, in this pressurization process, the cuff pressure Pc is sequentially detected based on the output signal from the oscillation circuit 33 and stored in the memory unit 42.

Note that as long as the equilibrium control target value V0 shows a value based on the arterial volume signal in the case where the internal pressure of the artery and the cuff pressure are in equilibrium, the present embodiment is not limited to such a detection method. For example, the present embodiment is not limited to a method for performing detection in the pressurization process as mentioned above, and detection may be performed in the depressurization process.

The parameter detection unit 103 stores the values of the direct current component of the arterial volume signal detected in the pressurization process in time series in the memory unit 42. The graph of the curve in (A) of FIG. 5 is detected, based on the data stored in the memory unit 42. The graph ((B) in FIG. 5) of the slope dV/dP is detected by differentiating the detected graph. All data of the detected graph is stored in a prescribed area of the memory unit 42.

The parameter detection unit 103 reads out the data of the graph in (B) of FIG. 5 from the memory unit 42, and detects the maximum value of the slope dV/dP based on the read data. In the case where the detected maximum value (slope dV/dP corresponding to equilibrium control target value V0) is taken as 100%, the arterial volume V corresponding to a rate of change less than or equal to a prescribed threshold value (e.g., 10%) relative to that rate of change (dV/dP) is detected, and the difference between the detected arterial volume V and the equilibrium control target value V0 is calculated. The difference is stored in the memory unit 42 as a control deviation target value dV. The parameters for servo control are thereby detected.

Here, although the control deviation target value dV is decided in accordance with the method of FIG. 5, subsequent processing can be similarly applied, even with values decided using the method of FIG. 6.

Constant Volume Control

The constant volume control unit 104 calculates the difference between the value of the arterial volume signal (direct current component of volume pulse wave) sequentially detected at the time of blood pressure measurement, and the equilibrium control target value V0 read out from the memory unit 42. The servo gain is decided while being updated, such that the calculated difference is less than or equal to the control deviation target value dV read out from the memory unit 42.

The decided servo gain is provided to the cuff pressure control unit 101. The cuff pressure control unit 101 controls the pump drive circuit 53 or the valve drive circuit 54 based on a control amount (voltage signal) conforming to the provided servo gain. In other words, the pump drive circuit 53 or the valve drive circuit 54 controls operation of the pump 51 or the opening and closing of the valve 52, such that the control deviation is less than or equal to the control deviation target value dV.

Operations at the time of Blood Pressure Measurement

Operations of the electronic sphygmomanometer 1 will be described.

Figure 7:
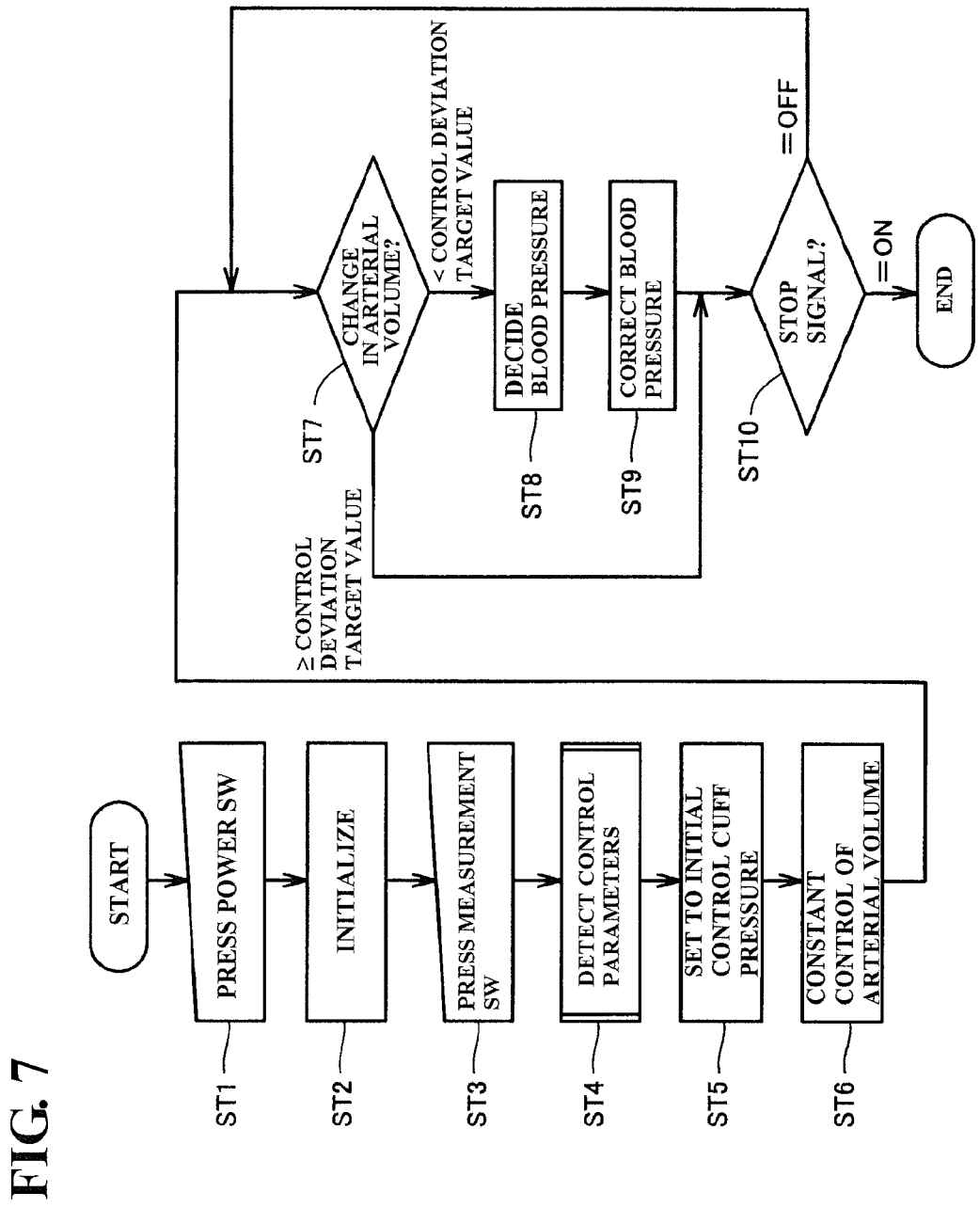
FIG. 7 is a flowchart for measuring blood pressure according to the embodiment.
Figure 8:
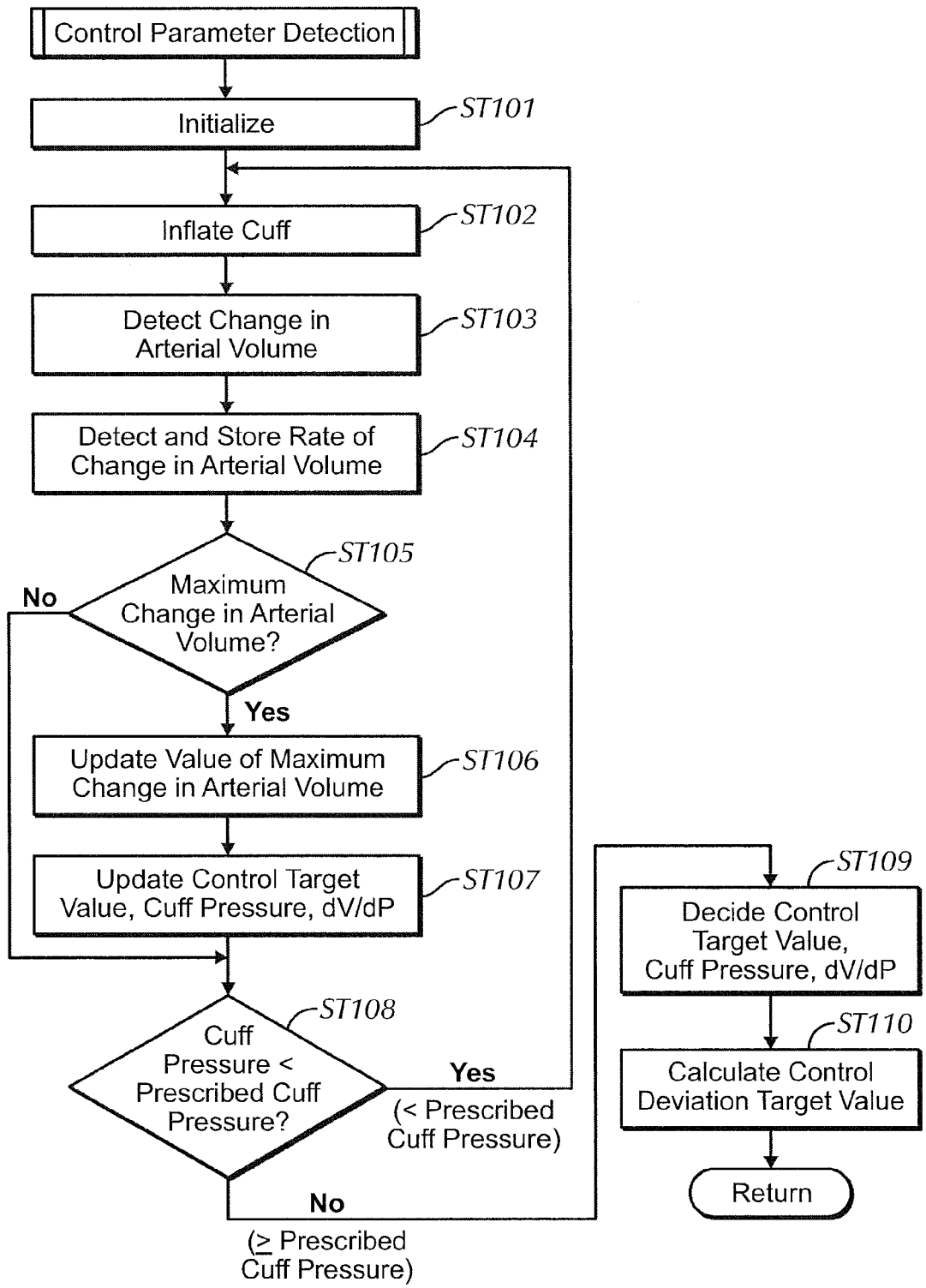
FIG. 8 is a flowchart for deciding control parameters according to the embodiment.

FIG. 7 is a main flowchart of blood pressure measurement processing, and FIG. 8 is a flowchart of control parameter detection. The processing shown in the flowchart is stored in the memory unit 42 in advance as a program, and the function of blood pressure measurement processing is realized by the CPU 100 reading out and executing this program.

Referring to FIG. 7, the CPU 100, having detected that the power switch 41A has been pressed by a user (step ST1), performs initialization processing (step ST2). Specifically, a prescribed area (hereinafter, "memory area") of the memory unit 42 is initialized, air in the air bladder 21 is exhausted, and 0 mm Hg correction of the pressure sensor 32 is performed. At this time, the cuff 20 has been placed on the measurement site.

Next, when the CPU 100 has detected that the measurement switch 41B has been pressed (step ST3), the cuff pressure control unit 101 is activated and pressurization of the measurement site is started.

Next, the parameter detection unit 103 detects the above-mentioned equilibrium control target value V0, control deviation target value dV, and the like (step ST4). The details of this processing will be discussed later with reference to FIG. 8.

The cuff pressure control unit 101 controls the cuff pressure so that the arterial volume V matches the equilibrium control target value V0. At this time, the cuff pressure is controlled so as to be set to an initial control cuff pressure Pcb, which will be discussed later (step ST5). Servo control is performed by the constant volume control unit 104 after the cuff pressure has been set to the initial control cuff pressure Pcb (step ST6).

Because the time for adjusting the servo gain can be shortened, enabling the time taken to decide blood pressure to be shortened, and blood pressure measurement to be performed without increasing the servo gain, that is, at a low servo gain, because of the cuff pressure Pc at the start of control thus being matched to the initial control cuff pressure at which the arterial volume V matches the equilibrium control target value V0 in the servo control, an air system that is able to control a high flow rate is not needed, and device miniaturization is not inhibited.

In the servo control period of steps ST7 to ST9, the constant volume control unit 104 calculates the difference between the average value of the arterial volume signal per pulse wave detected by the arterial volume detection circuit 74 and the equilibrium control target value V0 read out from the memory unit 42, and decides the servo gain such that the calculated difference is less than the control deviation target value dV read out from the memory unit 42. The cuff pressure control unit 101 controls the pump drive circuit 53 or the valve drive circuit 54 based on a control amount determined in accordance with the decided servo gain. In this way, feedback control of the cuff pressure Pc is repeatedly performed based on an arterial volume signal that is sequentially detected.

Specifically, the constant volume control unit 104 compares the difference (control deviation) between the value of the arterial volume signal detected by the arterial volume detection circuit 74 and the equilibrium control target value V0 with the control deviation target value dV (step ST7). When it is determined that the control deviation is greater than or equal to dV based on the comparison result, the processing transitions to step ST10 which will be discussed later, without blood pressure measurement being performed.

When it is determined that the control deviation is less than dV based on the comparison result, the processing transitions to the blood pressure measurement of step ST8.

In step ST8, the blood pressure decision unit 105 decides, as a provisional blood pressure value, the cuff pressure Pc detected when it is determined that the control deviation is less than the control deviation target value dV (step ST8).

Note that because the blood pressure measurement unit 102 sequentially detects the cuff pressures Pc based on the signal inputted from the oscillation circuit 33 and stores the detected cuff pressures Pc in a prescribed area of the memory unit 42 in time series in the period of steps ST5 to ST10, the cuff pressures Pc in the memory unit 42 can be searched, and the cuff pressure Pc detected when it was determined that the control deviation is less than the control deviation target value dV can be read out.

The correction unit 106 corrects the provisional blood pressure value and acquires an accurate blood pressure. Specifically, the blood pressure error Er serving as the correction value is calculated in accordance with "blood pressure error Er=control deviation/max(dV/dP)", using the control deviation and the slope max(dV/dP) (discussed later) read out from the memory unit 42. Because the control deviation is equivalent to the deviation between the arterial volume V and the equilibrium control target value V0, that is, the arterial volume that is not detected when the arterial volume V is the equilibrium control target value V0, "pressure equivalent to the deviation component" that is not included in the provisional blood pressure value is detected by dividing the control deviation by the slope max(dV/dP). The blood pressure error Er is thereby detected.

The blood pressure value after correction is calculated in accordance with "blood pressure value=provisional blood pressure value+error Er". The final blood pressure value is thereby calculated (measured).

The blood pressure after correction is recorded in the flash memory 43 in time series. Continuous blood pressure values are thereby acquired, and a blood pressure waveform is obtained as a result.

The measurement processing unit 106 may display information relating to decided blood pressure values on the display unit 40 during measurement. For example, the local minimum value and the local maximum value of the cuff pressure Pc per heartbeat may be displayed on the display unit 40 as the diastolic blood pressure and the systolic arterial pressure, respectively. Alternatively, a blood pressure waveform along the time axis may be displayed.

The measurement processing by the blood pressure measurement unit 102 is continued until a stop signal is turned on by the stop switch 41C being pressed, a prescribed time elapsing, or the like (step ST10).

When the stop signal has been turned on, the blood pressure measurement unit 102 records the blood pressure values (cuff pressures) recorded in the memory area in time series to the flash memory 43 or the recording medium 132 as measurement results.

Control Parameter Detection Processing

The details of the processing of step ST4 in FIG. 7 will be described, with reference to FIG. 8.

The processing flow of FIG. 8 consists of steps ST101 to ST110. Of these, steps ST102 to ST108 are equivalent to the process of increasing the cuff pressure Pc in which the arterial pressure-external pressure differential Ptr in (A) of FIG. 5 changes from "Ptr3" to "Ptr0". Steps ST102 and ST103 in the pressurization process are equivalent to the process for detecting the change in the arterial volume V shown by the solid line curve in (A) of FIG. 5. Step ST104 is equivalent to the process for detecting the slope dV/dP in (B) of FIG. 5. Steps S105 to S107 are equivalent to the process for detecting the maximum slope dV/dP in (B) of FIG. 5.

In the operations, first the parameter detection unit 103 initializes the memory area of the memory unit 42 for storing the maximum value (hereinafter, maximum ΔVmax) of the change in arterial volume, the arterial volume Vmax detected when the maximum ΔVmax is detected, the cuff pressure Pcb detected when the maximum ΔVmax is detected, and the slope dV/dP (hereinafter, slope max(dV/dP)) detected when the maximum Vmax is detected (ST101). A value 0, for example, is respectively set for the maximum ΔVmax, the arterial volume Vmax, the cuff pressure Pcb and the slope max(dV/dP) in the memory area as a result of initialization. In order to detect the equilibrium control target value V0, the arterial volume Vmax is detected.

Next, the parameter detection unit 103 increases the cuff pressure at a constant speed of 3 mm Hg/sec via the cuff pressure control unit 101 (ST102). In the pressurization process, the parameter detection unit 103 detects the arterial volume change ΔV every pulse wave (ST103). Also, the slope dV/dP is calculated every prescribed cuff pressure (e.g., every 3 mm Hg) at this time, and stored in time series in the memory unit 42 (ST104). The slope dV/dP calculated at this time is compared with the slope max(dV/dP) read from the memory unit 42, and it is determined whether the calculated slope dV/dP is the maximum based on the comparison result (ST105).

When it is determined that the condition "dV/dP>max(dV/dP)" is satisfied based on the comparison result (YES at step S105), the arterial volume Vmax, the maximum ΔVmax, the cuff pressure Pcb and the slope max(dV/dP) in the memory unit 42 are updated by being overwritten with the arterial volume V, the arterial volume change ΔV, the cuff pressure Pc and the slope dV/dP that are detected this time (ST106, ST107), and the processing transitions to step ST108. When it is determined that the condition "dV/dP≤max(dV/dP)" is satisfied based on the comparison result (NO at step S5105), the processing transitions to step ST108.

At step ST108, the parameter detection unit 103 compares the cuff pressure Pc with a prescribed pressure. When it is determined that the condition "cuff pressure Pc<prescribed pressure" is satisfied based on the comparison result (YES at step ST108), the processing returns to step ST102 and the subsequent processing is similarly repeated. When it is determined that the condition "cuff pressure Pc≥prescribed pressure" is satisfied based on the comparison result (NO at step ST108), the processing transitions to step ST109. The prescribed pressure at step ST108 can be any pressure at which a pulse wave can no longer be detected when the artery is compressed as a result of the pressurization, and denotes a pressure of 280 mm Hg, for example, in the present embodiment.

When the cuff pressure Pc indicates a pressure greater than or equal to the prescribed pressure as a result of such processing being repeatedly performed in the pressurization process, the arterial volume Vmax, the cuff pressure Pcb and the slope max(dV/dP) in the memory unit 42 respectively indicate the equilibrium control target value V0, the cuff pressure Pcb for matching the arterial volume with the equilibrium control target value V0 in (A) of FIG. 5, and the maximum value of the slope dV/dP in (B) of FIG. 5.

In step ST109, the arterial volume Vmax, the cuff pressure Pcb and the slope max(dV/dP) in the memory unit 42 are respectively decided as the equilibrium control target value V0, the initial control cuff pressure Pcb and a coefficient for a blood pressure correction operation.

In step ST110, the control deviation target value dV is calculated based on the slope dV/dP read from the memory unit 42, and stored in the memory unit 42.

The parameters used in order to correct the constant volume control (servo control) and the measured blood pressure are detected as described above.

According to the above blood pressure measurement processing, although the blood pressure error Er is included in the measured blood pressure due to the change in cuff pressure not being able to track the change in arterial volume perfectly in servo control because of allowing a control deviation, correcting the measured blood pressure using the blood pressure error Er enables accurate blood pressure values to be calculated.

Also, because accurate blood pressure can be calculated even when the change in cuff pressure cannot track the change in arterial volume perfectly, a pump 51 and a valve 52 that are capable of controlling a high flow rate are not needed. As a result, miniaturization of the electronic sphygmomanometer 1 can be achieved.

Comparison of Blood Pressure Before and After Correction

Figure 9:
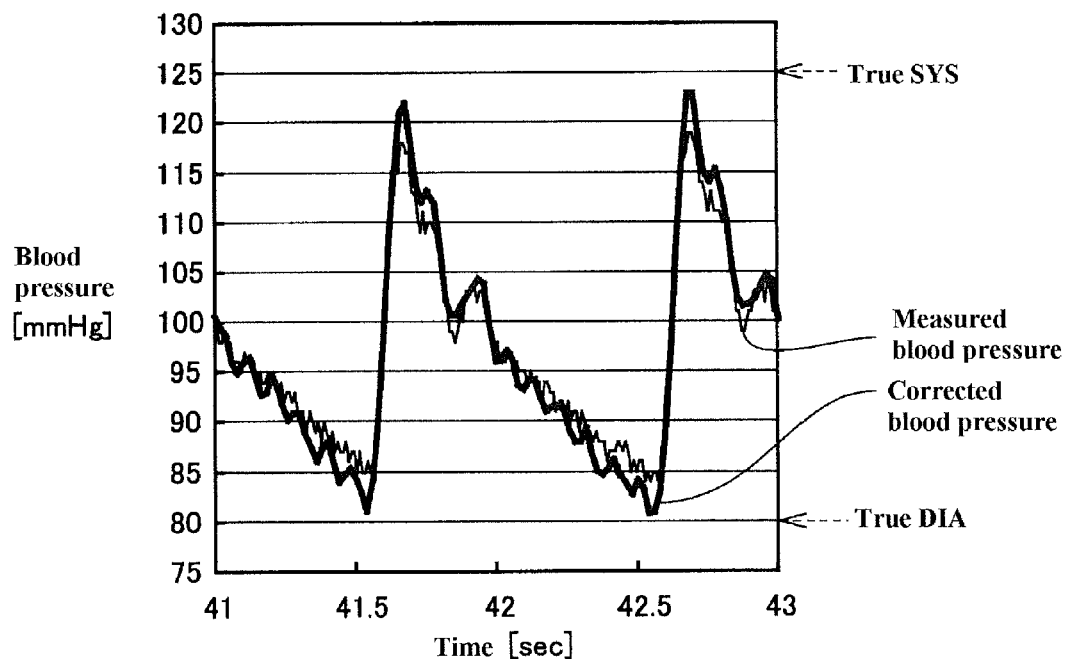
FIG. 9 is a diagram comparatively showing blood pressure waveforms before and after correction.
Figure 10:
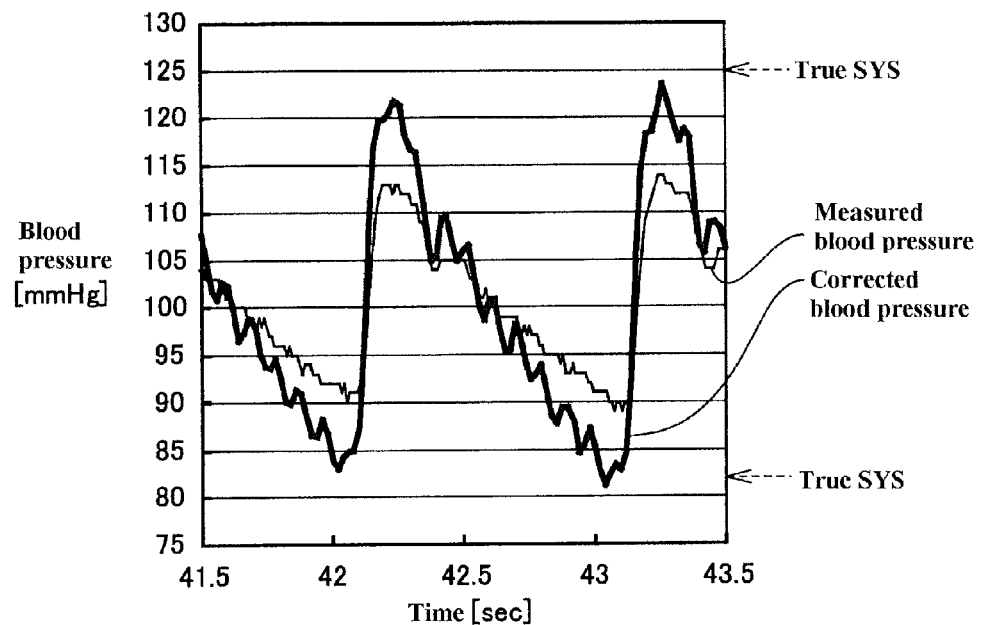
FIG. 10 is a diagram comparatively showing blood pressure waveforms before and after correction in the case of lowering a servo gain.

In FIG. 9 and FIG. 10, the results of comparing the blood pressure waveform after correction and the blood pressure waveform before correction that were detected in the case where the inventors measured the blood pressure of the upper arm in tests using the electronic sphygmomanometer 1 are shown with graphs. Here, the blood pressure waveform before correction denotes the waveform of the cuff pressure Pc.

In the graphs of FIG. 9 and FIG. 10, elapsed time (sec) of blood pressure measurement is on the horizontal axis, and blood pressure (mm Hg) is on the vertical axis. The thick line denotes the blood pressure waveform before correction, and the thin line denotes the blood pressure waveform after correction. In the graphs, the values of the true systolic arterial pressure SYS and the true diastolic blood pressure DIA are also indicated for the purpose of description.

It is clear from FIG. 9 that blood pressure values close to the true blood pressure values (systolic arterial pressure SYS, diastolic blood pressure DIA) can be measured as a result of correction.

In FIG. 10, test results are shown in the case where tests were performed after lowering the servo gain as compared with the case in FIG. 9 are shown. Other requirements and the parameters of the tests were the same as those of FIG. 9. Referring to FIG. 10, it is clear that even in the case where the servo gain is lowered, the blood pressure after correction is closer to the true blood pressure values (systolic arterial pressure SYS, diastolic blood pressure DIA) than is the blood pressure before correction. Accordingly, even in the case where a small pump 51 capable of controlling a low flow rate is used, blood pressure values close to the true blood pressure values can be measured, according to the measurement method of the present embodiment.

Blood Pressure Measurement Program

The blood pressure measurement method performed by the electronic sphygmomanometer 1 of the present embodiment can also be provided as a program.

Such a program can also be recorded with an optical medium such as CD-ROM (Compact Disc-ROM) or a computer-readable non-transitory recording medium such as a memory card, and provided as a program product. The program can also be provided by download via a network.

Note that the program according to one or more embodiments of the present invention may be a program that calls required modules in a prescribed arrangement at a prescribed timing, from among program modules provided as part of an operating system (OS) of a computer, and causes the called modules to execute processing. In this case, the above modules are not included in the program itself, and processing is executed in cooperation with the OS. A program that does not include such modules can also be included in the program according to one or more embodiments of the present invention.

Also, the program according to one or more embodiments of the present invention may be a program that is provided by being incorporated as part of another program. Modules included in the other program are also not included in the program itself in this case, and processing is executed in cooperation with the other program. Such a program incorporated in another program can also be included in the program according to one or more embodiments of the present invention.

A program product that is provided is executed after being installed in a program storage unit such as a hard disk. Note that the program product includes the program itself and the storage medium on which the program is stored.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE NUMERALS LIST

1 Electronic sphygmomanometer
10 Main body unit
20 Cuff
21 Air bladder
30 Air system
31 Air tube
32 Pressure sensor
33 Oscillation circuit
40 Display unit
41 Operation unit
41A Power switch
41B Measurement switch
41C Stop switch
41D Memory switch
42 Memory unit
43 Flash memory
44 Power supply
45 Clock unit
46 Interface unit
50 Adjustment unit
51 Pump
52 Valve
53 Pump drive circuit
54 Valve drive circuit
70 Arterial volume sensor
71 Light emitting element
72 Light receiving element
73 Light emitting element drive circuit
74 Arterial volume detection circuit
100 CPU
101 Cuff pressure control unit
102 Blood pressure measurement unit
103 Parameter detection unit
104 Constant volume control unit
105 Blood pressure decision unit
106 Correction unit
132 Recording medium

The invention claimed is:

1. An electronic sphygmomanometer comprising:
a cuff that is configured to be placed on a blood pressure measurement site;
a pressure detection unit that detects a cuff pressure representing a pressure inside the cuff;
a volume detection unit provided in the cuff that detects an arterial volume signal showing an arterial volume of the blood pressure measurement site in a process of changing the cuff pressure, wherein the arterial volume signal changes depending on a pulse wave associated with each heart beat;
a cuff pressure adjustment unit that adjusts the cuff pressure by pressurization and depressurization; and
a blood pressure measurement unit,
wherein the blood pressure measurement unit comprises:
a control target value detection unit that detects, as a control target value, a value of the arterial volume signal when an amplitude of the arterial volume signal detected by the volume detection unit indicates a maximum;
a rate-of-change detection unit that sequentially detects a rate of change in the arterial volume in the process of changing the cuff pressure, based on the arterial volume signal detected by the volume detection unit;
a control deviation detection unit that detects, as a control deviation, a difference between the value of the arterial volume signal and the control target value;
a servo control unit that performs servo control on the cuff pressure adjustment unit using a servo gain, such that the value of the arterial volume signal matches the control target value; and
a blood pressure decision unit that decides, as a blood pressure, the cuff pressure sequentially detected by the pressure detection unit in a period during which the servo control is performed, by correcting the cuff pressure using the control deviation and a rate of change that is deemed to be constant, and wherein the servo control unit updates the servo gain every pulse wave, such that the control deviation, which is the difference between the value of the arterial volume signal detected by the volume detection unit and the control target value, indicates a value that is less than a control deviation target value, which is the control deviation detected by the control deviation detection unit in a period during which the rate of change sequentially detected by the rate-of-change detection unit is deemed to be constant.

2. The electronic sphygmomanometer according to claim 1, wherein the blood pressure decision unit calculates a correction value, by dividing the control deviation by the rate of change that is deemed to be constant, and corrects the cuff pressure by adding the correction value to the cuff pressure.

3. The electronic sphygmomanometer according to claim 1, wherein the period during which the rate of change is deemed to be constant denotes a period during which a rate of change that is greater than or equal to a prescribed threshold is detected with respect to rates of change detected by the rate-of-change detection unit when the maximum value of the amplitude of the arterial volume signal is detected.

4. The electronic sphygmomanometer according to claim 1, wherein the period during which the rate of change is deemed to be constant denotes a period in which a difference in rates of change is less than or equal to a prescribed threshold, with respect to rates of change detected by the rate-of-change detection unit when the value of the arterial volume signal indicates the control target value.

5. The electronic sphygmomanometer according to claim 1, wherein the blood pressure measurement unit further comprises a detection unit that detects, as an initial control cuff pressure, the cuff pressure detected when the amplitude of the arterial volume signal detected by the volume detection unit is a maximum value, and wherein the servo control unit starts the servo control, such that the value of the arterial volume signal matches the control target value, after the cuff pressure is set to the initial control cuff pressure by the cuff pressure adjustment unit.

6. The electronic sphygmomanometer according to claim 1, wherein the process of changing the cuff pressure denotes a process of increasing the cuff pressure or a process of reducing the cuff pressure.

7. A blood pressure measurement program stored on a non-transitory computer readable recording medium for measuring blood pressure while detecting an arterial volume signal showing an arterial volume of a blood pressure measurement site in a process of changing a cuff pressure representing a pressure inside a cuff that is placed on the blood pressure measurement site, wherein the arterial volume signal changes depending on a pulse wave associated with each heart beat, the program causing a computer to execute the steps of:

detecting, as a control target value, a value of the arterial volume signal when an amplitude of the detected arterial volume signal indicates a maximum;

sequentially detecting a rate of change in the arterial volume in the process of changing the cuff pressure, based on the detected arterial volume signal;

detecting, as a control deviation, a difference between the value of the arterial volume signal and the control target value;

performing servo control on a cuff pressure adjustment unit using a servo gain, such that the value of the arterial volume signal matches the control target value; and deciding, as a blood pressure, the cuff pressure sequentially detected in a period during which the servo control is performed, by correcting the cuff pressure using the control deviation and a rate of change that is deemed to be constant, and wherein the step of performing servo control comprises updating the servo gain every pulse wave, such that the control deviation, which is the difference between the value of the detected arterial volume signal and the control target value, indicates a value that is less than a control deviation target value, which is the control deviation detected in a period during which the sequentially detected rate of change is deemed to be constant.

* * * * *